US011039956B2

(12) United States Patent
Böhme et al.

(10) Patent No.: US 11,039,956 B2
(45) Date of Patent: Jun. 22, 2021

(54) OPHTHALMOLOGICAL LASER THERAPY DEVICE

(71) Applicant: Carl Zeiss Meditec AG, Jena (DE)

(72) Inventors: Beate Böhme, Großpürschütz (DE); Marco Hanft, Jena (DE); Thomas Nobis, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 583 days.

(21) Appl. No.: 15/561,894

(22) PCT Filed: Mar. 24, 2016

(86) PCT No.: PCT/EP2016/056527
§ 371 (c)(1),
(2) Date: Sep. 26, 2017

(87) PCT Pub. No.: WO2016/156190
PCT Pub. Date: Oct. 6, 2016

(65) Prior Publication Data
US 2018/0125708 A1 May 10, 2018

(30) Foreign Application Priority Data
Mar. 30, 2015 (DE) .......................... 102015205696.1

(51) Int. Cl.
*A61F 9/008* (2006.01)

(52) U.S. Cl.
CPC .......... *A61F 9/008* (2013.01); *A61F 9/00802* (2013.01); *A61F 9/00821* (2013.01);
(Continued)

(58) Field of Classification Search
CPC ............... A61F 2009/00897; A61F 2009/0087
(Continued)

(56) References Cited

U.S. PATENT DOCUMENTS 5,997,141 A 12/1999 Heacock
6,347,244 B1 * 2/2002 Dubnack ................. A61F 9/008
600/476
(Continued)

FOREIGN PATENT DOCUMENTS

DE         699 00 340 T2      6/2002
DE   10 2011 006 085 A1      9/2012
(Continued)

OTHER PUBLICATIONS

English translation of PCT International Preliminary Report on Patentability and Written Opinion for International Application No. PCT/EP2016/056527, dated Oct. 12, 2017, 8 pages.
(Continued)

*Primary Examiner* — Gary Jackson
*Assistant Examiner* — Zahed Kabir
(74) *Attorney, Agent, or Firm* — Patterson Thuente Pedersen, P.A.

(57) ABSTRACT

An ophthalmological laser therapy device including a laser system, an x-y scanner, collecting optics and a z-scanner. The invention also relates to a method for processing a tissue of an eye by a therapeutic laser beam of an ophthalmological laser therapy device. The invention provides an ophthalmological laser therapy device and a corresponding method which permit, with minimal engineering complexity, a very quick positioning of the laser spot in a large volume region, in particular in a large x-y region perpendicular to the optical axis. The problem is also solved by a method for processing a tissue of the eye or a material located in an eye using an ophthalmological laser therapy device, wherein each subsection of the tissue of the eye is processed using a corresponding positioning or the device for the adjustable redirecting of the laser beam in an image field of the collection optics.

18 Claims, 5 Drawing Sheets

(52) U.S. Cl.
CPC ...... *A61F 9/00825* (2013.01); *A61F 9/00827* (2013.01); *A61F 2009/0087* (2013.01); *A61F 2009/00851* (2013.01); *A61F 2009/00853* (2013.01); *A61F 2009/00868* (2013.01); *A61F 2009/00872* (2013.01); *A61F 2009/00874* (2013.01); *A61F 2009/00887* (2013.01); *A61F 2009/00889* (2013.01); *A61F 2009/00897* (2013.01)

(58) Field of Classification Search
USPC .......................................................... 606/5
See application file for complete search history.

(56) References Cited

U.S. PATENT DOCUMENTS

| | | |
|---|---|---|
| 6,635,051 B1 | 10/2003 | Hohla |
| 2005/0286019 A1* | 12/2005 | Wiltberger ............ A61B 3/0091 351/211 |
| 2006/0195076 A1* | 8/2006 | Blumenkranz ..... A61F 9/00812 606/4 |
| 2009/0131921 A1* | 5/2009 | Kurtz .................. A61F 9/00825 606/4 |
| 2011/0028948 A1* | 2/2011 | Raksi ...................... A61F 9/008 606/4 |
| 2011/0028951 A1 | 2/2011 | Raksi et al. |
| 2011/0116040 A1* | 5/2011 | Biernat .................. A61F 9/008 351/206 |
| 2011/0184395 A1* | 7/2011 | Schuele ................. A61F 9/008 606/5 |
| 2012/0316544 A1 | 12/2012 | Horvath et al. |
| 2013/0274725 A1* | 10/2013 | Rathjen ............... A61F 9/00806 606/5 |
| 2014/0094711 A1* | 4/2014 | Sondermann ........ A61B 3/0008 600/558 |
| 2014/0288539 A1* | 9/2014 | Bischoff ............. A61F 9/00836 606/4 |
| 2015/0051591 A1* | 2/2015 | Hanebuchi .............. A61F 9/008 606/4 |

FOREIGN PATENT DOCUMENTS

| | | |
|---|---|---|
| DE | 10 2011 006085 A1 | 9/2012 |
| DE | 10 2011 085 046 A1 | 4/2013 |
| EP | 2 111 831 A1 | 10/2009 |
| EP | 2 664 309 A1 | 11/2013 |
| WO | WO 2006/074 469 A2 | 7/2006 |

OTHER PUBLICATIONS

PCT International Search Report and Written Opinion for International Application No. PCT/EP2016/056527, dated Jun. 9, 2016, 13 pages.
English translation of PCT International Search Report for International Application No. PCT/EP2016/056527, dated Jun. 9, 2016, 2 pages.
DE Search Report for 102015205696.1, dated Dec. 17, 2015, 11 pages.

* cited by examiner

OPHTHALMOLOGICAL LASER THERAPY DEVICE

RELATED APPLICATIONS

This application is a National Phase entry of PCT Application No. PCT/EP2016/056527 filed Mar. 24, 2016 which application claims the benefit of priority to German Application No. 102015205696.1, filed Mar. 30, 2015, the entire disclosures of which are incorporated herein by reference.

FIELD OF THE INVENTION

The invention relates to an ophthalmological laser therapy device having a laser system for generating a therapy laser beam, an x-y scanner for deflecting the therapy laser beam perpendicular to the optical axis of the ophthalmological laser therapy device, a collecting optics for mapping the therapy laser beam in an image field, and a z scanner for shifting the focal point of the therapy laser beam in a z direction along the optical axis. The invention also relates to a method for treating a tissue of the eye or another material in an eye, in particular for producing an incision in a tissue of the eye by means of a therapy laser beam through photodisruption, ablation or coagulation with such an ophthalmological laser therapy device.

BACKGROUND

DE 10 2011 006 085 A1 describes an ophthalmological laser therapy system for using the radiation of a femtosecond (fs) laser on eyes. The laser therapy system described therein contains a lens, from which a focused beam exits toward the eye. Furthermore, the lens is either capable itself of shifting the focal point or focal plane from the cornea into the lens of the eye, thus causing a z shifting of the focal plane along the optical axis, or the lens is a part of a collecting optics that contains at least one lens group, by varying the positions of which, such a z shifting of the focal plane is caused. A further shiftable z scanning lens enables a further z scanning, wherein the respective possible scanning range of the z scan for a work step determines the respective possible defocusing range, and an x-y deflection unit of the laser therapy system, disposed between the shiftable z scanning lens and the lens, enables a corresponding shifting in the x and y directions, thus a shifting perpendicular to the optical axis. Such an x-y deflection unit can contain, for example, two mirrors that can be tilted in relation to one another, between which a pupil optics composed of two collecting lenses is disposed in one embodiment variation.

In order to bring the focal point from the cornea of the eye into the lens of the eye, the z shifting by the lens, or by a displaceable lens group of the lens, is used. The lens remains stationary during the direct treatment of the cornea or the lens of the eye, however, and the focal point of the laser is moved in the respective region of the eye with the x-y deflection unit and the z scanning lens.

For technical reasons, it has not been possible to focus the laser on a desired location, i.e. the cornea or the lens of the eye, at precisely one point: there is still a certain expansion of the spot size or spot diameter at the focal point. A laser spot is also referred to in this context. Both terms shall be used more or less synonymously herein, with the knowledge that when the focal point of a laser beam is delineated, this also naturally has a corresponding expansion, and thus depicts a laser spot.

For the desired purposes, such as the treatment of the cornea or lens of an eye through photodisruption, spot diameters of only a few micrometers must be obtained for each x-y position of the laser spot, wherein a typical spot diameter is less than 3 μm in the cornea, or less than 5 μm in the lens tissue of the eye, respectively. This requires that the lens exhibits a significant technological complexity: it is known that the technical complexity, with otherwise the same requirements for the imaging quality, increases with the Lagrange invariant, which is proportional to the product of the numerical aperture and the diameter of the image field, which must simultaneously be well lit via the optics.

In order to obtain a spot diameter $D\sim\lambda/NA$ of 3 μm on the cornea of the eye, a minimum aperture of ca. $NA_H=0.33$ must be obtained when $\lambda\sim1$ μm. With a desirable diameter of the image field to be simultaneously lit via the optics of $F_H=14$ mm for the treatment of the cornea of the eye, the Lagrange invariant is obtained from the product of the minimum aperture and the image field diameter for $LW_H \sim NA_H F_H=4.62$. However, for the treatment of the lens of the eye with an $NA_L=0.33$, a Lagrange invariant of $LW_L\sim2.3$ is obtained with an image field diameter $F_L=7$ mm that is typical for the lens. With a minimum aperture of $NA_L=NA_H=0.2$, obtained from a less critical maximum spot diameter of 5 μm, Lagrange invariants of $LW_H=2.8$ and $LW_L=1.4$ are obtained for the treatment of the cornea or the lens, respectively.

The varying of the focus in z, thus in the z scanning range or defocusing range, by the amounts $Z_L=2$ mm for a treatment of the lens of an eye, and $Z_H=0.5$ mm for a treatment of the cornea of an eye, results in additional complexity. When this complexity is delineated by a further factor, and defines a "three-dimensional" Lagrange invariant $LR_H \sim NA_H F_H Z_H$, then for $NA_H=NA_L=0.2$, $LR_L=2.8$ is obtained for the treatment of the cornea, and a three-dimensional Lagrange invariant $LR_H=1.4$ is obtained for the lens. For a numerical aperture of 0.33, the "three-dimensional" Lagrange invariants $LR_H=2.31$ or $LR_L=4.6$ are obtained. The technological complexity for a lens that maps the volume in question with limited diffraction then increases with the Lagrange invariant. If the technological complexity is to be reduced, this can be achieved through reducing the defocus range and/or reducing the diameter of the image field that must also be lit at the same time.

This problem is solved in US 2012/03165544 A1 by a femtosecond laser system for treating the eye, in which a movement of the projecting lens in relation to the light source of the laser takes place. The laser light arriving from a light source is modified in terms of its divergence via a variable telescope, enabling a z scanning. It is directed toward a decentered optics with a large beam diameter, and toward the eye via a dichroic mirror. By rotating an optics located in a fixture about the axis of the fixture, which is parallel but not identical to the axis of symmetry of the optics, the laser spot delineates a circuit on the eye. Furthermore, positioning elements are used on the dichroitic mirror, in order to move the laser spot in the x and y directions. The eye is lit thereby, either directly or via a contact lens. With an additional unit, an aiming beam is directed toward the eye, in order to align the therapy beam in relation to the eye.

This assembly has various disadvantages: on one hand, a portion of the lighting is blocked, resulting in performance losses at the eye, and disruptive light in the device. On the other hand, the components that are to be moved are so large and heavy that a scanning speed in the hertz or kilohertz range requires an extremely high engineering complexity, such that it is hardly possible to obtain cutting times of less than 10 seconds, in particular less than 3 seconds, and ideally, cutting times of less than or equal to 1 second, which are necessary for a treatment without a fixed coupling between the eye and the treatment device, and without a constant alignment to an aiming beam.

For this reason, contact lenses are used in laser therapy systems, e.g. for cataract surgery, as adapters for orienting and fixing the eye in relation to the treatment device, thus to the laser therapy system, as is described, for example, in DE 103 49 296 A1. The eye is subjected to a suction by application of a vacuum, and fixed in place in relation to the device thereby. In this manner, it is possible to treat the eye for substantially longer treatment periods, but the system is more complex, on one hand, and on the other hand, a laser therapy treatment without such an adapter and the association coupling is more pleasant and gentler for the patient. In particular, the elimination of this coupling between the eye and the therapy system also simplifies the manipulation of the system for the physician.

Similar solutions to that in US 2012/0316544 A1 for minimizing the Lagrange invariants of the optics are also described in EP 2 664 309 A1 and DE 10 2011 085 046 A1. These solutions all require a lateral movement of the optics in front of the eye, in order to reach all of the positions of the laser spot necessary for the respective treatment.

Embodiments of the present invention specify an ophthalmological laser therapy device and a corresponding method for enabling a very quick positioning of the laser spot in a large treatment volume range with very little technological complexity, and in particular to ensure a treatment in a large x-y range perpendicular to the optical axis.

SUMMARY OF THE INVENTION

An ophthalmological laser therapy device for treating a tissue region of an eye and/or a material located in an eye by application of a laser beam has a laser system for generating a therapy laser beam. Normally, this is a pulsed laser beam, such that a generation of correspondingly higher energies in a focal range of the laser beam is possible, which enables, e.g. an incision in a desired tissue region of the eye by separating the tissue by photodisruption, a removal of tissue or other material in the eye through ablation or a bonding or other modification of tissue and/or material through coagulation.

The ophthalmological laser therapy device also has an optical axis, which is defined as the axis of the rotational symmetry of the lens elements that are used between two deflection elements, e.g. scanners or mirrors, or between laser sources and the first deflection element or between the last deflection element and the "target object," and changes its direction at the deflection elements when they are in an initial position. The tilting of the deflection elements, in particular scanners or tilting mirrors, from their initial position causes a deflection of the therapy laser beam away from this optical axis.

In the beam path of the therapy laser beam, the ophthalmological laser therapy device comprises an x-y scanning unit, configured for deflecting the therapy perpendicular to the optical axis. The x-y scanning unit thus enables a deflection of the therapy laser beam inside a treatment plane defined by an x and a y direction that are perpendicular to the optical axis. This treatment plane is then normally positioned in a tissue of an eye or in a material located in the eye, which can be a foreign body in particular. With this positioning, the treatment plane defined by the x and y axes then runs basically parallel to a plane of the pupil of the eye that is to be treated, wherein this can deviate from a precise parallelism to the plane of the pupil by a few degrees when it is possible for the components to deviate from an initial position through the use of the solution according to the invention.

The x-y scanning unit thus shifts, or scans, the laser spot parallel to this pupil plane of the eye that is to be treated. Advantageously, it enables a high scanning speed through a corresponding construction that avoids moving complex and heavy systems. The x-y scanning unit can be designed as an overall system. Alternatively, it can also contain sub-systems, which may be spatially separated from one another.

In the beam path of the therapy laser beam, the ophthalmological laser therapy device further comprises a collecting optics. The collecting optics contains one or more lens elements and is configured to map the therapy laser beam in an image field. This image field is disposed in the work plane. The size of this image field is determined by the collecting optics.

If the collecting optics contains numerous lens elements, as is advantageous for the mapping properties, in particular their variability, then these lens elements are combined in one or more lens groups. For a collecting optics that contains numerous lens groups, these lens groups can also be disposed such that they are spatially separated from one another.

The collecting optics has an axis of symmetry, which, in the region of the collecting optics, is identical to the optical axis of the ophthalmological laser therapy device. The collecting optics itself cannot be moved in the x or y direction.

Moreover, the ophthalmological laser therapy device comprises a z scanning device in the beam path of the therapy laser beam for shifting the focal point of the therapy laser beam in a z direction along the optical axis. Such a z scanning device can be an autonomous device or it can be contained in one of the elements specified above or in the following.

The sequence of the arrangement of the elements described so far in the beam path of the therapy laser beam of the ophthalmological laser therapy device is not fixed or important.

According to the invention, the ophthalmological laser therapy device further includes an adjustable laser beam deflection device, which is disposed in the beam path downstream of the collecting optics. "Disposed downstream" is to be understood thereby as being disposed in the beam path of the laser system, following the collecting optics. In an example embodiment, the adjustable laser beam deflection device is also disposed downstream of the z scanning device. The adjustable laser beam deflection device may be designed as an integral unit, but it can also contain numerous interacting optical elements in order to deflect the laser beam in the desired manner.

The adjustable laser beam deflection device alters the direction of the course of the laser beam. For this, the adjustment of the deflection can be selected, e.g. by selecting the angle of deflection. Normally, the device is thus brought into a desired deflection position, and deflects the therapy laser beam focused by the collecting optics, or, optionally, another laser beam, such as an aiming beam for making adjustments, or an OCT beam for examining a desired therapy region on the eye, at the desired deflection angle. As a result, it shifts the individual image field of the collecting optics in the working plane. Consequently, the possible working field of the collecting optics that can be obtained through the individual image field of the collecting optics and its possible deflection range that can be obtained through the adjustable laser beam deflection device, and in which, consequently, a tissue of the eye or another material located in the eye can be treated, is significantly expanded.

The ophthalmological laser therapy device according to the invention is thus distinguished in that the image field of the collecting optics can be positioned in a work field that is larger than the image field of the collecting optics through the use of the adjustable laser beam deflection device.

The adjustment of the deflection of the laser beam is, for example, fixed in position during the respective laser therapy step or laser therapy sub-step. For this, the adjustable laser beam deflection device contains structures for fixing the adjusted deflection of the laser beam, such that during a laser therapy step, or a laser therapy sub-step, respectively, the region of the tissue of the eye that can be reached via the respective individual image field of the collecting optics and a deflection that has been set, is treated.

As explained above, a minimizing of the technological complexity takes place according to the invention through a reduction of the Lagrange invariants of the system, thus a simplification of the lens, a correspondingly small diameter of the image field of the lens, or in general, a small image field of the mapping optics or collecting optics. This leads in turn to the necessity of an additional movement, in order to be able to position the laser spot in the entire volume range necessary for treating an eye. With the ophthalmological laser therapy device according to the invention, through the use of the adjustable laser beam deflection device downstream of the collecting optics in interaction with the x-y scanning unit, the respective moving components for deflecting in the x or y direction are small, and can be moved very quickly compared to solutions according to the prior art. These high speeds are possible because it is not necessary to move entire lenses or lens groups at these speeds.

A capsulorhexis, for example, can be carried out with the solution according to the invention in less than a second. Furthermore, it enables a fragmenting of the eye lens and further incisions on the cornea in similar time periods. Because of the high speeds, a "docking" of the eye, thus a fixing of the eye to the ophthalmological laser therapy device, is unnecessary.

Typical maximum spot diameters of the laser spot in the image field of the collecting optics, e.g. 3 to 5 μm, can be maintained thereby. Furthermore, a working field can be obtained through the combined individual image fields of the collecting optics when the deflection of the therapy laser beam is set by the adjustable laser beam deflection device, which is at least largely comparable to image fields of ophthalmological laser therapy devices according to the prior art.

It is also particularly advantageous that by using the adjustable laser beam deflection device, the (individual) image field of the collecting optics can be placed in a variable manner, and can thus be optimally adjusted to the region of an eye tissue that is to be treated, and additional movements of the optics or optical system during the laser therapy can be avoided in many cases, which cannot be avoided, for example, in US 2012/0316544 A1 due to the movement specifications therein, which are set in order to be able to reach the entire region of the eye tissue that is to be treated.

In order to coordinate the different movements of the x-y scanning unit, the z scanning device, the adjustable laser beam deflection device, and, if applicable, other moving units, to one another, the use of a control unit is advantageous. This control unit can have an integral design, or be composed of numerous parts. Ideally, it can access all of the moving units, as well as other units of the ophthalmological laser therapy device that require control, and can link the movements, if applicable, to other therapy parameters, e.g. parameters of the laser system for generating the therapy laser beam.

In an example embodiment of the ophthalmological laser therapy device, the adjustable laser beam deflection device contains a partially or fully reflective surface, for example a partially or fully reflective planar surface, and two axes that are perpendicular to one another, wherein the partially or fully reflective surface can be pivoted about one, or preferably both, of the axes, which are perpendicular to one another. By pivoting the partially or fully reflective surface, a shifting of the laser spot is caused in the x and/or y direction, independently of and in addition to the possibilities of the x-y scanning unit and the collecting optics.

Advantageously, an ophthalmological laser therapy device in which the partially or fully reflective surface causes an adjustment of the deflection of the laser beam, comprises a beam splitter plate, in particular a dichroitic beam splitter plate, or a mirror, in particularly a dichroitic mirror.

The adjustable laser beam deflection device of the ophthalmological laser therapy device can furthermore contain at least one refractive optical element having spherical surfaces, which is disposed downstream of the partially or fully reflective surface. In particular, this can be a lens element, which is not, however, part of the collecting optics. This optical element can serve, on one hand, to form a defined boundary surface in relation to the eye, or to optimize the optical transition to the eye. Such a refractive optical element can also, on the other hand, fulfill the function of a z scanning. In this case, the refractive optical element can necessarily be shifted in the z direction, and ideally, movement in the x-y plane is also provided for.

The movement of such a refractive optical element is for example coupled directly to the pivoting of the partially or fully reflective surface. A mechanical, permanent connection between the partially or fully reflective surface and the refractive optical element is particularly beneficial, such that the refractive element is pivoted together therewith. These movements are preferably controlled by the control unit.

In an example embodiment of the ophthalmological laser therapy device, the laser system is a femtosecond (fs) laser system. By way of example, it can be a femtosecond (fs) laser system having a wavelength of ca. 1 μm, which generates pulses having a pulse duration of a few 100 femtoseconds, and having pulse energies in the μJ range, preferably between 3 and 10 μJ, wherein the pulse energy is sufficient for destroying a material in the eye at the selected position of the laser spot, thus to separate or modify it, normally by means of photodisruption. This material can be eye tissue, e.g. the cornea, lens capsule, lens or other parts, or a previously implanted material, e.g. IOL material. Alternatively, the laser system can also emit radiation in a narrow band range in another wavelength range, and cause a change in the material through absorption, e.g. of a dye previously injected in the eye.

It is furthermore advantageous when the ophthalmological laser therapy device contains a collecting optics in a first alternative, which can be shifted in the z direction as a unit. In a second alternative, the ophthalmological laser therapy device comprises a collecting optics, which contains one or more lenses that can be displaced in the z direction, thus along the optical axis, wherein these numerous displaceable lenses can be displaced independently of one another, or as a collective lens group. This collecting optics that can be displaced in the z direction as a whole or as individual lenses or lens groups, either fulfills only the function of the z scanning device, such that no further elements are required for the z scanning device, or is formed in addition to another optics that can be displaced in the z direction, between the laser system and the scanners.

It is preferable, however, to have a collecting optics that can be displaced as a whole or as individual lenses or lens groups in addition to a further z scanning device. In this case, a further z scanner, or scanning lens, is disposed upstream or downstream of the x-y scanning unit, which moves the laser spot on the eye in only a very small z range, which is smaller than 0.25 mm or, for example, smaller than 0.1 mm.

In an inexpensive embodiment of the ophthalmological laser therapy device according to the invention, the collecting optics is corrected for an image field having a diameter of less than 7 mm, for example for an image field having a diameter in a range of 4 to 7 mm. The collecting optics can be configured thereby as a double gauss lens, and be designed such that the large aperture side faces the eye. The image field can be either planar or curved, such that the focus can lie on the axis with a larger z value than with a diameter between 4 mm and 7 mm.

The x-y scanning unit of an ophthalmological laser therapy device can advantageously contain, in a first alternative, two galvanometer scanners disposed directly behind one another, or, in a second alternative, a biaxial scanner, or even two scanners having pupil mapping capabilities in another alternative. These advantageous alternatives of an x-y scanning unit can all deflect the therapy laser beam simply: a displacement or movement of structurally heavy systems, e.g. collecting optics, is not necessary, such that x-y scanning units of this type can function substantially more quickly and precisely, and scanning frequencies of 100 Hz can be easily obtained.

The ophthalmological laser therapy device according to the invention contains a scanning lens for focusing the therapy laser beam in most of the embodiments, and is configured to generate an intermediate image of the image field in an intermediate image plane between the collecting optics and the scanning lens, wherein the scanning lens focuses the light coming from the x-y scanning unit in the intermediate image plane. In particular, the course of the main beam in this intermediate image can deviate from the telecentricity.

If an intermediate image is generated in an ophthalmological laser therapy device according to the invention, then the collecting optics is configured to generate an image field in the working plane, thus, e.g. in a plane in a tissue of the eye, in a reduction of the intermediate image by at least a factor of two. An image field that is a reduction of this intermediate image by a factor of four is preferred.

With an axial displacement of this collecting optics, or parts of the collecting optics, for the purpose of a z scan, thus a displacement in the z direction, the mapping scale between the intermediate image and the image field of the collecting optics changes in the working plane, thus the image field on the eye. Thus, a variation of the scale of the reduction from 4× to 4.5× is possible.

In order to be able to correct the scale of the mapping of the intermediate image, and thus compensate for the change in the reduction of the intermediate image through the collecting optics during a z scan, or during the change to the z position of the laser spot, at least one scanning angle of the x-y scanning unit can be corrected with a correction factor in a preferred ophthalmological laser therapy device. This is achieved through a corresponding activation of the scanner. The activation of the scanner then takes place via a control unit, which can calculate appropriate correction factors, and correct the scanning angle therewith.

For example, an ophthalmological laser therapy device is configured for decoupling light into an observation beam path. The observation beam path can contain, for example, an observation unit such as a slit lamp or a surgical microscope, and enables direct observation of the laser therapy of the eye, without a time delay. In order to implement the decoupling of the light into the observation beam path, the adjustable laser beam deflection device can contain a beam splitter, in particular a dichroitic beam splitter.

An ophthalmological laser therapy device according to the invention preferably contains a device for generating an aiming beam, which is used for focusing and laterally directing the laser therapy beam. For this, an aiming beam, which is generated, for example, with light having a second wavelength from the range of visible light, is superimposed on the therapy laser beam in a collinear manner, such that it also experiences all of the deflection and redirection steps applied to the therapy laser beam, which is visible along its path as well as in the target region due to its wavelength.

For a better alignment of the therapy laser device using an aiming beam, which functions with light from the visible wavelength range, the aiming beam focus and the therapy beam focus in the eye can be axially offset to one another in an ophthalmological laser therapy device according to the invention.

The axial offsetting is thus an offsetting in the z direction, thus along the optical axis. The thickness of the lens capsule, for example, can be compensated for by such an axial offsetting, such that the focusing on the cloudy, scattering eye lens is possible, but the lens capsule is treated, which in turn makes for better visibility and is thus easier to align.

In a method according to the invention, for treating a tissue of an eye and/or a material located in the eye by application of a therapy laser beam, e.g. for creating an incision in a tissue of the eye through photodisruption with an ophthalmological laser therapy device according to the invention, first, the adjustable laser beam deflection device is fixed in a position while the therapy laser beam is switched off, which deflects the therapy laser beam such that a first sub-region of the tissue of the eye that is to be treated and/or the material located in the eye, is located in the image field of the collecting optics. If desired, additional diagnosis steps can then also take place in this image field, e.g. in order to determine and set necessary incision depths by OCT. The first sub-region of the tissue of the eye and/or the material located in the eye is then treated with the therapy laser beam switched on, by use of a series of quick x-y scans by the x-y scanning unit, and a single slow z scan.

During these quick x-y scanning procedures, thus during the treatment of the respective accessible sub-region of the tissue of the eye and/or the material located in the eye, the adjustable laser beam deflection device normally remains in a fixed position. It is only used for positioning the sub-region of the tissue or the material that is to be treated prior to initiating the therapy irradiation.

"Switched on therapy laser beam" means that the therapy laser beam exhibits the corresponding focusing and energy for treatment in principle during the treatment step, e.g. in order to be able to cause an incision through photodisruption in the tissue of the eye or in a material located in the eye, or to be able to remove the material through ablation, or to be able to alter tissue or materials through coagulation, and that the therapy laser beam also causes this, depending on the therapy program, in this sub-region, in corresponding to its x-y position and its z position, but it can be briefly interrupted during the quick x-y scans and in certain z positions of the slow z scan, if an incision is not to be generated at a corresponding position in the x, y and z axes that the therapy beam must pass through during its scan, or if no other type of treatment is to take place at this position.

After completion of the treatment of the first sub-region of the tissue of the eye, and/or the material located in the eye, that is to be treated, the therapy laser beam is again switched off, and a further sub-region of the tissue of the eye, and/or the material located in the eye, is brought into the image field of the collecting optics by changing the position of the adjustable laser beam deflection device, and the renewed setting of this changed position. In this next fixed position of the adjustable laser beam deflection device, this further sub-region of the tissue of the eye, and/or the material located in the eye, is treated with the therapy laser beam switched on.

The two aforementioned steps for positioning the adjustable laser beam deflection device and the treatment of a sub-region of the tissue of the eye, and/or the material located in the eye, by quick x-y scans and a slow z scan with the adjustable laser beam deflection device in a fixed position, are carried out for further sub-regions of the tissue of the eye, and/or the material located in the eye, until the tissue of the eye, and/or the material located in the eye has been fully treated in the intended manner, thus, e.g. until the incision has been completed in the lens, capsule and corneal tissue of the eye.

In order to treat a larger treatment field through successive treatment steps in numerous sub-regions, the partially or fully reflective surface can also be moved further, in a quasi-static manner through a very slow pivoting in comparison to the x-y scanning movement of the x-y scanning unit, wherein the control device applies appropriate correction factors to the movements of the scanning unit, such that a desired treatment pattern is obtained in the eye, wherein the control unit temporarily interrupts the therapy laser beam. In this manner, an increased treatment speed is obtained for the region that is to be treated. Because there is a higher tendency to error in the positioning of the sub-regions, and due to the greater chance that the eye may move, although this variation is possible, it is not preferred. Furthermore, it is not possible in this mode to carry out any intermediate additional examination steps, e.g. a control examination by OCT.

Many incisions or other forms of treatment in a tissue of the eye, and/or in a material located in the eye, only require small treatment fields, because they are carried out in a very limited local area. Thus, a small image field of the collecting optics of an ophthalmological laser therapy device is sufficient. In an advantageous embodiment of the method according to the invention, it is possible to avoid a multi-step solution in these cases, in that with a maximum expansion of the tissue of the eye, and/or the material located in the eye, that is to be treated, which is smaller than a diameter of the image field of the collecting optics, the adjustable laser beam deflection device is fixed in a position, such that all of the tissue or other material of the eye that is to be treated is located simultaneously and entirely within the image field of the collecting optics.

BRIEF DESCRIPTION OF THE DRAWINGS

The present invention shall now be described on the basis of exemplary embodiments. Therein.

DETAILED DESCRIPTION

Figure 1:
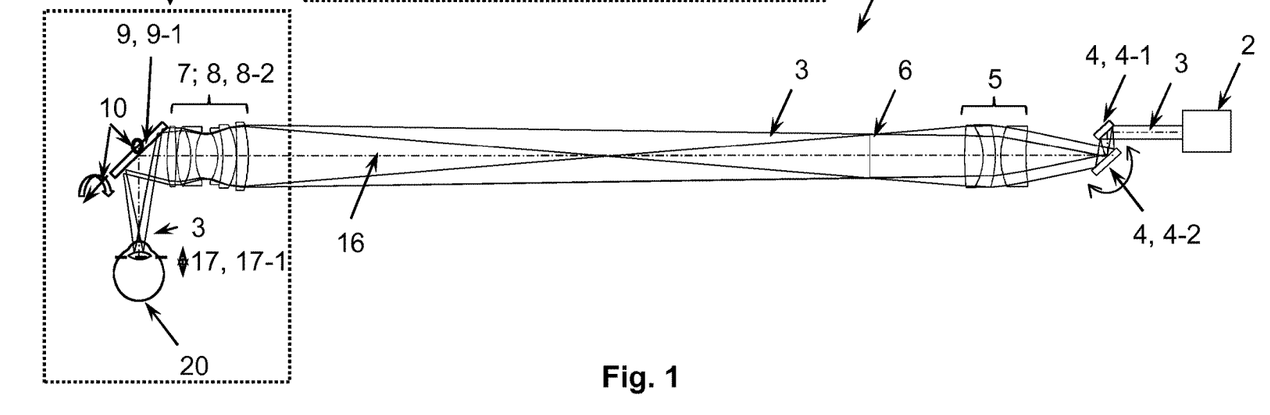
FIG. 1 shows a first exemplary embodiment of an ophthalmological laser therapy device according to the invention.

A first example embodiment of an ophthalmological laser therapy device 1 according to the invention is shown in FIG. 1. A femtosecond laser system 2 generates a laser beam 3, which is deflected to a scanning lens 5 via an x-y scanning unit 4, which contains two galvanometer scanners 4-1, 4-2 disposed directly behind one another, one of which is used for the x scan and the other is used for the y scan. The scanning lens 5 focuses the therapy laser beam 3 at an intermediate image 6 in an intermediate image plane. A mapping of the intermediate image 6 into a (single) image field 17-1 of the (entire) treatment field 17 in a working plane in the eye 20 takes place via a collecting optics 7, which is composed here of numerous lenses disposed in a lens group, wherein an adjustable laser beam deflection device 9, 9-1, which contains a pivoting mirror and is disposed downstream of the collecting optics 7, deflects the image field 17-1 of the collecting optics 7, in which the therapy laser beam 3 can move during the quick x-y scanning by the two galvanometer scanners 4-1, 4-2 into the desired region of the treatment field 17 for treating the eye 20. The pivoting mirror can pivot about two axes 10. By pivoting the pivoting mirror about one or both of the axes 10 and the subsequent fixing the pivoting mirror in this position, the desired deflection of the therapy laser beam 3 is set to this desired sub-region of the tissue of the eye 20 that is to be treated, prior to starting the laser therapy step.

The collecting optics 7, 8, 8-2 can move as a whole in the z direction in this simplest embodiment variation, whereby the focal point of the therapy beam 3 in the eye 20 can be shifted along the optical axis 16, thus in the z direction, and thus the image field 17-1 of the collecting optics 7 can be shifted from an inner tissue of the eye 20 into an outer tissue of the eye 20. In this manner, the collecting optics simultaneously forms the z scanning device. This possibility of a shifting of the focal point of the therapy laser beam 3 in the z direction is used prior to the laser therapy step for setting a starting depth in a tissue of the eye 20, as well as for a simultaneous z shifting of the spot during the therapy. The z positioning of the laser spot takes place thereby slowly in comparison to the x-y movement as a consequence of the quick movement of the x-y scanner, such that the laser spot delineates a spiral-shaped path, e.g. having a diameter of 6 mm and a depth of 0.25 mm for a capsulorhexis. In this embodiment variation, having just one z scan by the collecting optics, both the Lagrange invariant as well as the "3-dimensional" Lagrange invariant defined above are reduced to a minimum, because the lens 5 is only used in exactly one z plane, and the axial shifting of the spot through the movement of the optics 7 corresponds to the depth mapping scale, such that here as well, only one z plane is used in each case, in a manner similar to the focusing of a photographic lens.

Figure 3:
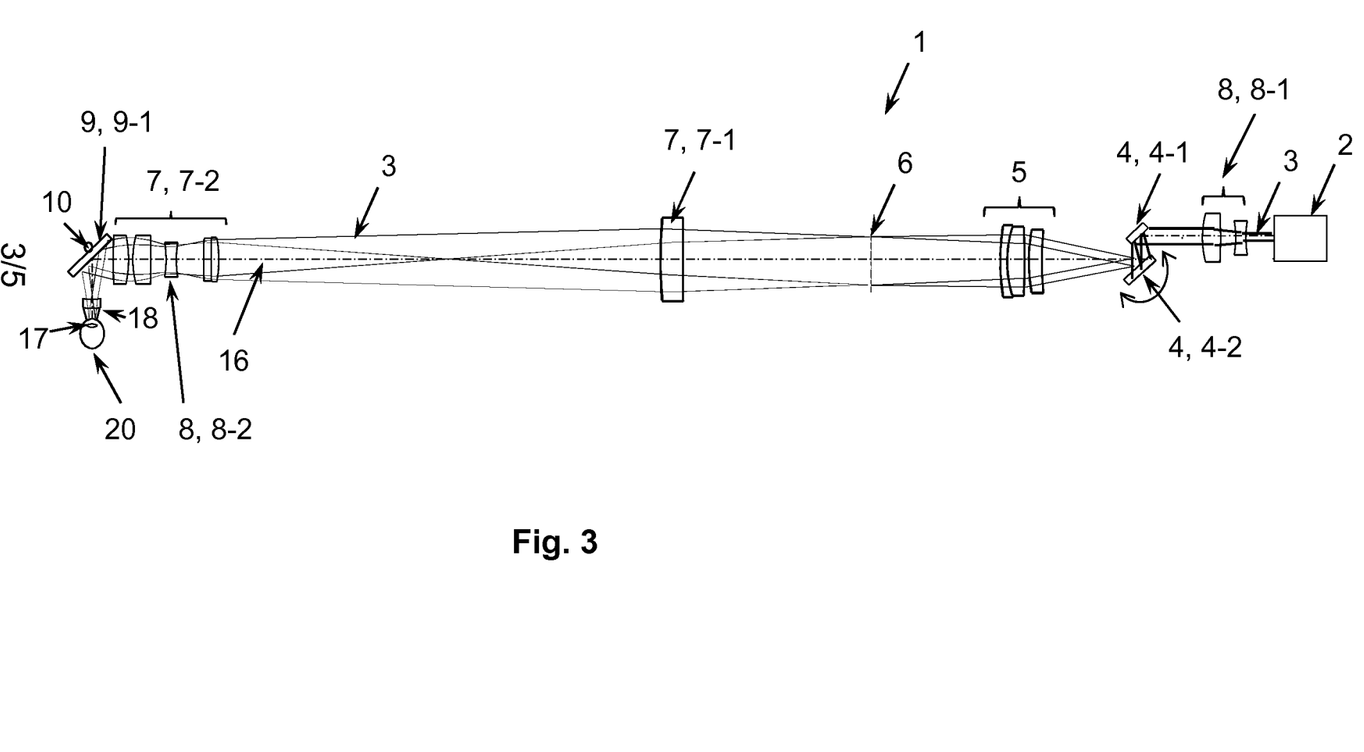
FIG. 3 shows a third exemplary embodiment of an ophthalmological laser therapy device according to the invention.

Alternatively, a z scanner can also be used during the therapy, between the therapy laser source and the x-y scanners, as is depicted in FIG. 3. However, the lenses 5 and 7 must also be configured in this case for the corresponding z range and the "3-dimensional" Lagrange invariant that is increased thereby.

During the quick x-y scanning process of the laser therapy step inside the image field 17-1 of the collecting optics 7 in the working plane, the adjustable laser beam deflection device 9, 9-1, and thus the pivoting mirror, remains fixed in place, and is used only for positioning the sub-region of the tissue that is to be treated, prior to initiating the therapy irradiation. As long as the spatial region, in which a material of the eye 20 is to be treated, lies within the possible working field 17, which is reached via the pivoting mirror by "pivoting" the image field 17-1 of the collecting optics 7, but is larger than the initially treated image field 17-1, the pivoting mirror is repositioned after treating this first position of the image field 17-1, and a next image field is treated, which is likewise a part of the working field 17.

Figure 1A:
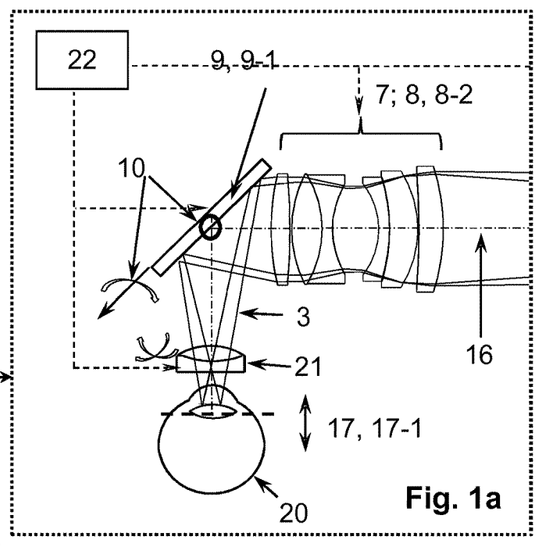
FIG. 1a shows a variation on the first exemplary embodiment of an ophthalmological laser therapy device according to the invention.

FIG. 1*a* shows a variation of the first example embodiment of an ophthalmological laser therapy device 1 according to the invention in an enlarged detail from FIG. 1: while no change is made to the assembly of the laser system 2, the galvanometer scanner 4-1, 4-2, the scanning lens 5, the collecting optics 7, which contains or depicts a z scanning device 8, 8-2 as a result of its overall movement along the optical axis, i.e. in the z direction, and the pivoting mirror 9, 9-1, an additional refractive optical element in the form of a lens element 21 is disposed downstream of the pivoting mirror, which, like the pivoting mirror 9-1, is part of the adjustable laser beam deflection device 9. This lens element 21 can move in the z direction as well as in the x-y plane. The movements of the lens element 21, as well as the movements of the pivoting mirror 9, 9-1 and the movements of other moving parts of the ophthalmological laser therapy device 1, such as, e.g., the movements of the collecting optics 7, 8, 8-2 along the optical axis, are coordinated via a control unit 22. As a result, the movements of the lens element 21 can be aligned with the movements of the pivoting mirror 9-1.

It is, however, particularly simple and advantageous when the pivoting mirror 9-1 and the lens element 21 are connected to one another in a fixed manner. In particular, the lens element 21 can be pivoted together with the pivoting mirror, when it is rotated, with a connection in which the optical axis of the lens element 21 intersects with the pivot point of the pivoting mirror. Because the lens element 21 can move in the z direction, there is the possibility of an additional z scan.

Figure 2:
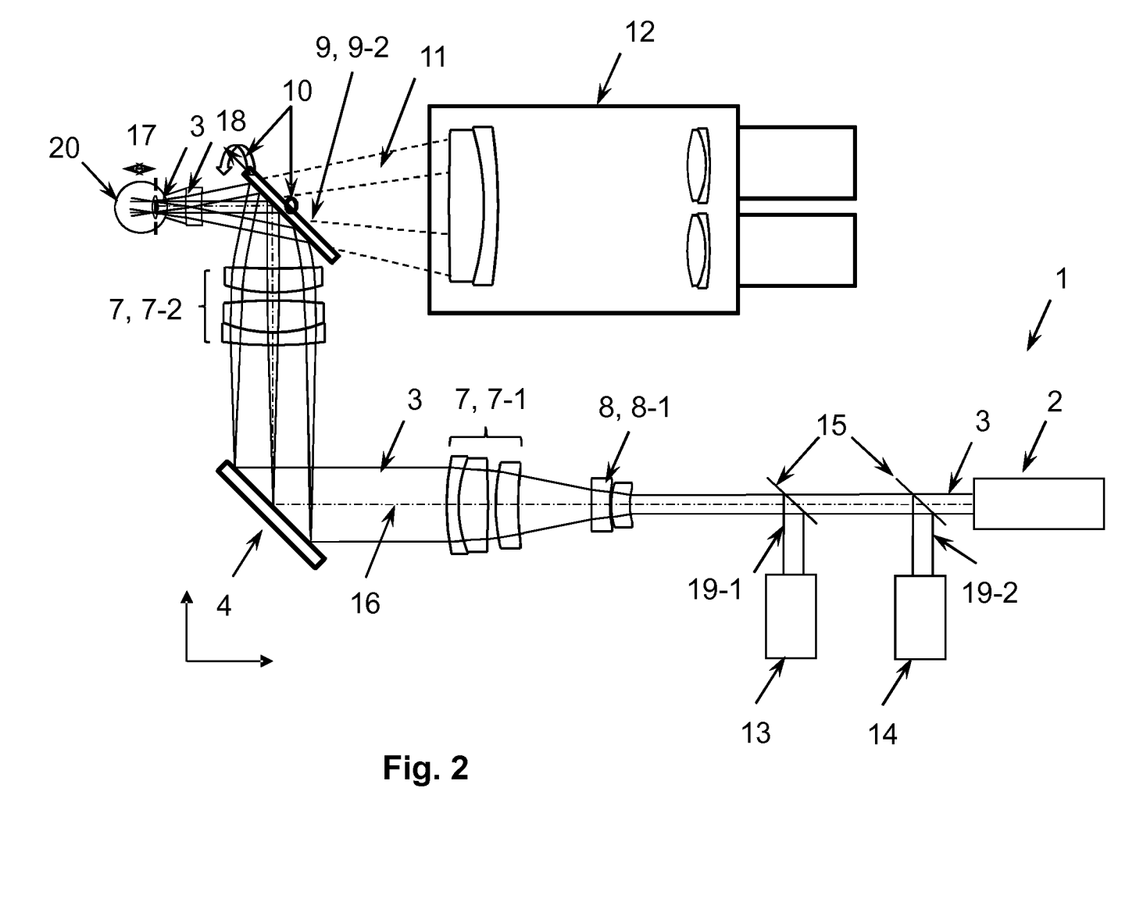
FIG. 2 shows a second exemplary embodiment of an ophthalmological laser therapy device according to the invention.

FIG. 2 shows a second exemplary embodiment of an ophthalmological laser therapy device 1 according to the invention. Here as well, a femtosecond laser system 2 generates the therapy laser beam 3. This first strikes a z scanning device 8, 8-1. This z scanning device 8, 8-1 is the only device in this second exemplary embodiment that enables a scanning along the z direction, thus along the optical axis. The therapy laser beam 3 subsequently arrives at the x-y scanning unit 4 via a first lens group 7-1 of the collecting optics 7, which is permanently disposed in the beam path, this x-y scanning unit 4 being a biaxial scanner, which accordingly serves simultaneously to scan in both scanning directions x and y. The x-y scanning unit 4 first directs the therapy laser beam 3 further through a second lens group 7-2 of the collecting optics 7, which is likewise permanently disposed in the beam path, to a device 9, 9-2 for adjusting the deflection of the laser beam. The device 9, 9-2 for adjusting the deflection of the laser beam then directs the therapy laser beam 3 in turn through a contact lens, or a patient interface 18 filled with liquid, merely placed on the eye 20 of a patient, such that the eye 20 is consequently not affixed on the ophthalmological laser therapy device 1, into the desired sub-region of the eye 20 that is to be treated with the therapy laser beam 3.

For this, the device 9, 9-2 for adjusting the deflection of the laser beam contains in turn two pivot axes 10. After setting the position by rotating about one or both pivot axes 10, making it possible to light the desired sub-region of the eye 20, such that the image field 17-1 of the collecting optics 7, 7-1, 7-2 is brought into alignment with the desired sub-region that is to be treated, this position is fixed, and a corresponding laser therapy step is carried out. In the case of this second exemplary embodiment, the device 9 for adjusting the deflection of the laser beam contains a dichroitic beam splitter 9-2. This enables, on one hand, as was already the case in the first exemplary embodiment, the deflection of the therapy laser beam 3 into the desired sub-region of the eye 20, and on the other hand, it allows an observation beam in the visible light range coming from the eye 20 to pass through the beam splitter 9-2 without reflection, and thus to be decoupled into an observation beam path 11. The observation beam is registered by an observation unit 12, in this case a surgical microscope, such that the laser therapy step can be observed while it is being carried out. Instead of the visible light, another wavelength range differing from that of the therapy laser beam, e.g. in a wavelength range of 700 nm to 900 nm, can be used for observation, if detection takes place with a CCD camera instead of the visual observation.

Due to the high speed, however, this is not the primary concern the observation unit 12. Instead, it serves for the preparation of the laser therapy step. Thus, the examination beam, e.g. an OCT laser beam 19-1 from the near infrared range, can be coupled into the beam path of the therapy laser beam 3 via a dichroitic mirror used as a beam splitter 15, in order to examine the eye prior to the laser therapy step. The eye can be observed with the surgical microscope during this examination, as long as an examination beam from the range of visible light is used.

Moreover, an aiming laser beam 19-2 having a wavelength from the range of visible light can be generated with a device 14 for generating an aiming laser beam 14, and coupled in turn into the beam path of the therapy laser beam 3 via a beam splitter 15, here as well, a dichroitic mirror. The therapy laser beam 3, the wavelength of which lies in the infrared range in this exemplary embodiment, can be directed with the aid of the aiming laser beam 19-2, while being observed with the surgical microscope. Furthermore, adjustments can be carried out with regard to the depth of the focal point of the therapy laser beam 3 in the eye 20, with regard to the starting point of the x-y scan and the z scan for the laser therapy step, and with regard to the desired sub-region that is to be treated on the eye 20. These adjustments are then implemented via the corresponding positioning of the device 9, 9-2 for adjusting the deflection of the laser beam prior to starting the laser therapy step.

FIG. 3 depicts a third example embodiment of an ophthalmological laser therapy device 1 according to the invention, which substantially corresponds to the first example embodiment. However, a collecting optics 7 is used here, the lenses of which are not disposed in a lens group: the collecting optics 7 contains a first lens element 7-1 in this case, which is located in the beam path of the therapy laser beam 3 at a substantial spacing in front of a lens group 7-2, and is disposed there in a fixed manner. The therapy laser beam has a collimated course, or exhibits a lower divergence here, between the lens element 7-1 and the lens group 7-2. The lens group 7-2 contains, in turn, just one single lens element 8, 8-2 that can be displaced in the z direction for a z scan, while the other lenses of the lens group 7-2 are disposed in a fixed manner in the beam path of the laser therapy beam 3. The displacement of the lens elements 8, 8-2 causes a change in the focal length of the collecting optics 7, and in turn, an axial shifting of the laser spot on the eye 20.

In one variation of the third example embodiment of the ophthalmological laser therapy device 1 according to the invention, which is not shown here, the entire lens group 7-2 can also be disposed such that it can be displaced. A further z scanner can be inserted between the laser system 2 and the x-y scanner 4, which, however, is less preferred due to the higher "3-dimensional" Lagrange invariant.

Furthermore, a contact lens 18 is used in the exemplary embodiment of FIG. 3, which, however, is merely placed on the eye 20 of a patient: the eye 20 is not affixed to the ophthalmological laser therapy device 1 by this contact lens 18. The contact lens 18, or another optical element fulfilling the same function at this location, serves only to form a defined boundary surface, and thus generates a more optimal optical transition to the eye 20.

The deflection into the desired sub-region of the eye 20 by the device 9, 9-1 for adjusting the deflection of the laser beam only takes place in the x direction, in contrast to the first example embodiment, because the device 9 for adjusting the deflection of the laser beam, which contains a dichroitic mirror 9-1, as in the first example embodiment, has only one pivotal axis 10.

Figure 4:
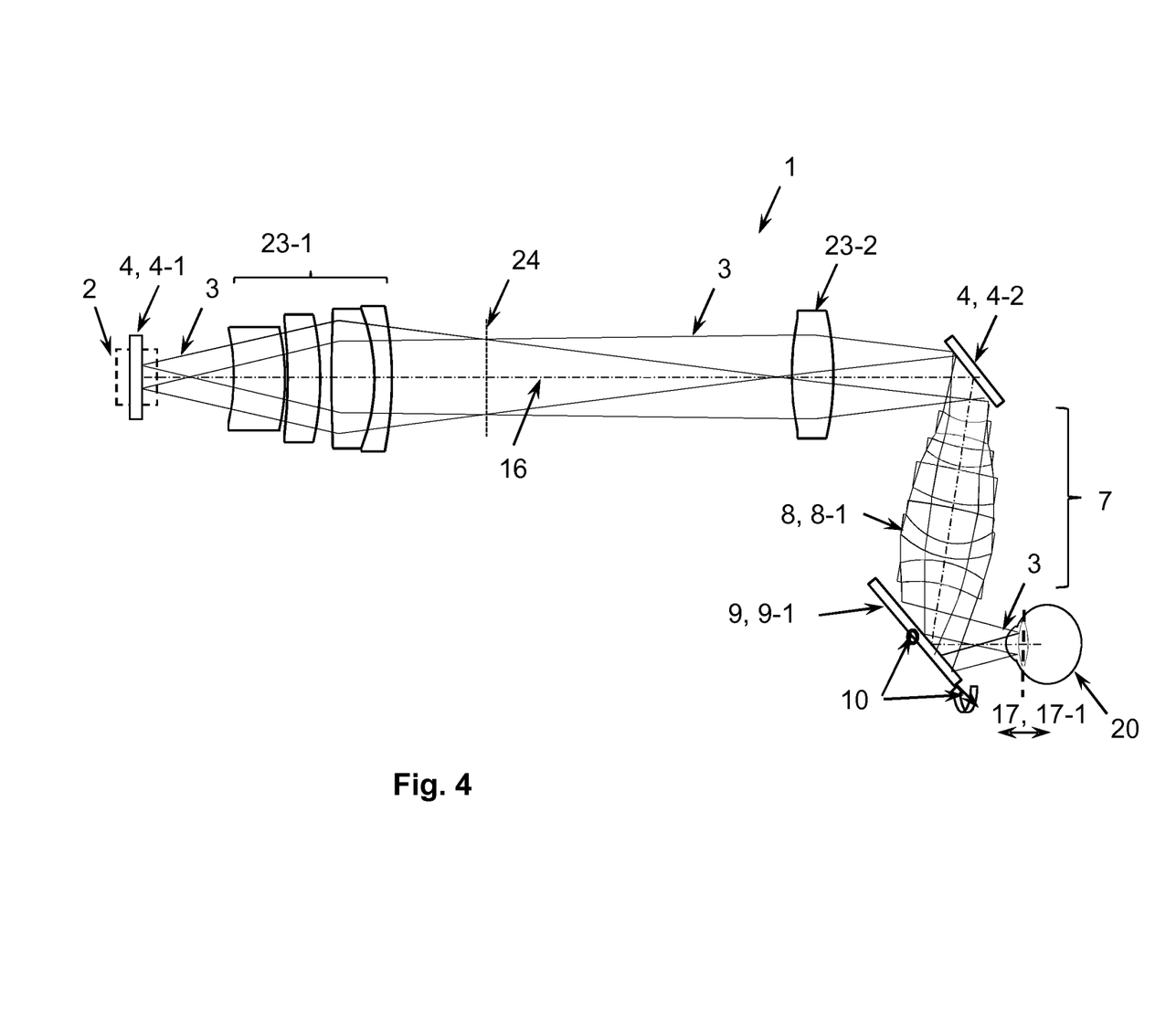
FIG. 4 shows a fourth exemplary embodiment of an ophthalmological laser therapy device according to the invention.

FIG. 4, in turn, shows a fourth example embodiment, having substantial differences to the example embodiments described above. In this example embodiment, the x-y scanning unit 4 has two spatially separated scanners 4-1, 4-2 having two-part pupil mapping implemented by the lens groups 23-1 and 23-2, and an intermediate image of the pupil mapping 24. The therapy laser beam 3, generated in the laser system 2, first strikes a y scanner 4-1, subsequently passes through the pupil relay, and the two lens groups 23-1 and 23-2 with the intermediate image 24, and strikes the x scanner 4-2, through which it is then directed to the collecting optics 7, which contains at least one axially displaceable lens 8, 8-2, and is thus configured as a zoom lens. The therapy laser beam 3 is subsequently directed into the sub-region of the eye 20 that is to be treated by use of the device 9 for adjusting the deflection of the laser beam, which in this case contains, in turn, a mirror 9-1 that can be pivoted about two axes 10, wherein in this case, in turn, a contact lens is not used.

Figure 5:
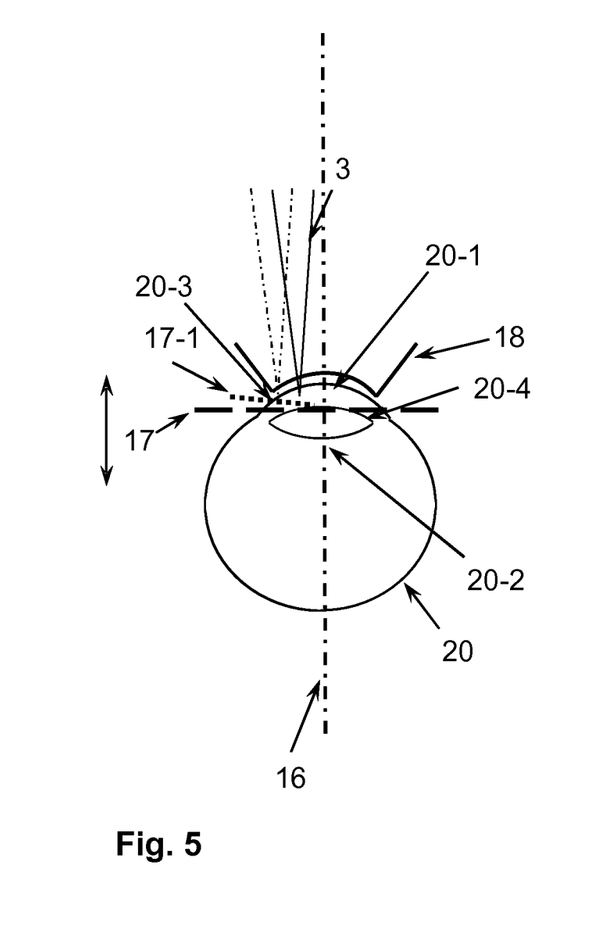
FIG. 5 shows a first exemplary application of the use of an ophthalmological laser therapy device according to the invention.

In a first application example for the use of an ophthalmological laser therapy device 1 according to the invention by a corresponding method, a capsulorhexis, thus an opening of the front lens capsule 20-4, the generation of the access incision, as well as further incisions for astigmatism corrections on the cornea 20-1, are depicted in FIG. 5.

After the eye 20 of a patient has been brought into position for treatment, and a contact lens 18 is placed thereon, which does not, however, fix the eye 20 in place, the focus of the collecting optics 7, which has been corrected for an image field 17-1 of 7 mm, is first adjusted to the desired starting position prior to starting the laser therapy treatment, e.g. symmetrical to the optical axis of the eye, 50 μm behind the lens capsule 20-4.

After setting this focus position, the therapy beam 3, normally a femtosecond laser beam, is switched on, wherein, due to the high scanning speed, it can be assumed that during the short treatment period, eye movements remain small enough that they have no effect on the results, in contrast to a capsulorhexis carried out with an ophthalmological laser therapy system according to the prior art, and it is not necessary to couple, i.e. "dock," the eye 20 on the ophthalmological laser therapy system 1 according to the invention.

After switching the therapy laser beam 3 on, a quick x-y scanning takes place with the galvanometer scanners 4-1, 4-2, which form the x-y scanning unit 4 of the laser therapy device 1 according to the invention. For the capsulorhexis, they are shifted in particular in phase-shifted sinusoidal oscillations, such that the laser spots lie in circular paths in the lens capsule 20-4 of the eye 20, which are delineated with frequencies of greater than 20 Hz, e.g. with a frequency of 100 Hz. In order to now obtain a capsulorhexis, e.g. an axially displaceable lens 8, 8-1 of the collecting optics 7 is moved once, at a lower speed, in the z direction, such that the laser spots pass over the z range of <250 μm necessary for a capsulorhexis.

In the next step, the image field 17-1 of the collecting optics 7 is shifted by the pivoting of the mirror 9-1 about an axis 10 inside the working field 17 into an outer-axial corneal tissue region for the access incision 20-3. In the new position of the image field 17-1, a laser therapy can then in turn take place through the movement of the scanners 4-2 and 4-1 as well as through the axial displacement of the lens 8-1 of the collecting optics 7.

Because the corneal tissue region 20-3, in which the x-y scanning for access incisions must take place for the intraocular lens implantation, has a significantly smaller diameter than 7 mm, with an appropriate initial positioning of the adjustable laser beam deflection device 9, in this case a dichroitic mirror 9-1 that can be pivoted about two axes 10, the diameter of the image field 17-1 of the collecting optics 7 is sufficient for executing the access incision in a single step.

In the same manner, further treatment steps can be carried out, e.g. on other parts of the cornea, in the trabecular, on the rear lens capsule, or in the vitreous body. A pulse laser having pulses in the ms range can also be used here for ablation or coagulation.

Figure 6:
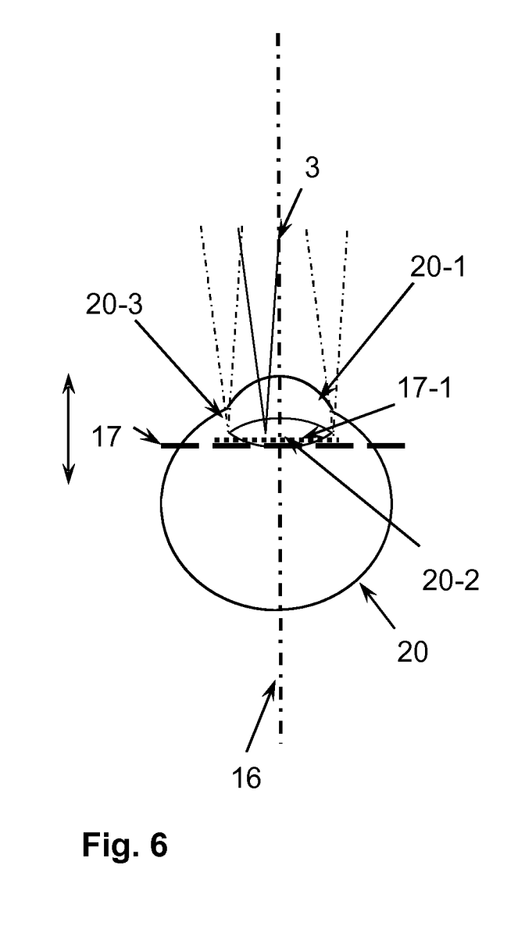
FIG. 6 shows a second exemplary application of the use of an ophthalmological laser therapy device according to the invention.

For a lens fragmentation by application of laser radiation, a similar approach to that selected for the capsulorhexis and creation of an access incision depicted in FIG. 5 is selected in a second application example for the use of an ophthalmological laser therapy device according to the invention that is depicted in FIG. 6.

After the eye 20 of a patient has then been brought into a treatment position, but the eye 20 is not fixed in position and remains without a contact lens, the focus of the collecting optics 7, which is corrected for an image field 17-1 of 7 mm, is first adjusted to the desired starting position in the lens tissue 20-2 of the eye 20, which, in this case, is located in the immediate proximity to the rear lens capsule, prior to starting the laser therapy treatment.

After setting this focus position, the therapy laser beam 3 is switched on, which in turn is generated by a femtosecond laser system 2, and a quick x-y scan is initiated, in that the galvanometer scanners 4-1, 4-2 of the x-y scanning unit 4 are activated individually or collectively, or with an appropriate phase shift, such that incisions generated through photodisruption can take place in arbitrary directions, thus in the x-y direction, the y-z direction, diagonally, or in other directions. During the quick x-y scan, the focus position of the therapy laser beam 3 is moved in turn to the front lens capsule through a slow z scanning. A single slow z adjustment only means that it is slow in relation to the x-y scan. With an x-y scanning speed of, e.g. 100 Hz and 100 necessary x scans in the lens 20-2 of the eye 20, the z variation can thus take place in 1 second. Because higher x scanning speeds are also technically possible, incisions can thus be made in the lens 20-2, in particular in less than 1 second.

In order to then reach a boundary region 20-3 of the cornea 20-1 of the eye 20 after a capsulorhexis or a lens fragmentation, e.g. in order to carry out additional incisions with the femtosecond therapy laser beam 3 for an astigmatism correction, the device 9, 9-1 for adjusting the deflection of the laser beam is positioned such that the boundary region 20-3 of the cornea 20-1 of the eye 20 ends up in the image field 17-1 of the collecting optics 7. For this, the dichroitic mirror 9-1 that can be pivoted about two axes 10 is tilted, and after aiming it, i.e. directing or checking the direction of the therapy laser beam 3, a quick scanning is initiated. In a similar manner, the image field 17-1 can be shifted to another location in the eye 20 that is to be treated.

Thus, the collecting optics 7 do not need to light a field of 11 mm on the cornea 20-1: the image field of 5 mm to 7 mm, necessary for the eye lens 20-2, or the capsulorhexis, is sufficient, which reduces the technological complexity for the collecting optics 7. This reduced image field 17-1 is positioned as needed by the operator, prior to initiating the therapy radiation. Locations can thus be reached on the cornea 20-1, which have, e.g., a diameter of 13 mm, i.e. ultimately the working field 17 that can be obtained therewith is even larger than with solutions from the prior art, which obtain a large single image field 17-1 with a great deal of engineering effort, which, however, cannot be shifted, thus reducing the working field 17 to the size of the image field 17-1 of the collecting optics 7.

In order to compensate for the changes to the mapping scale of the collecting optics 7, e.g. a lens, which is obtained with a z variation through a z scanning, or through the single shifting of a focus position along the optical axis 16 over the scanning angle of the x-y scanning unit 4, a correction factor is applied to at least one of the scanning angles. When the collecting optics 7 has, e.g. a focal length of 45 mm for the first example embodiment of the ophthalmological laser therapy device 1 according to the invention, and reduces the intermediate image 6 in the eye at a scale of 4 to 1, then with a focal length modification by 1%, i.e. a change in the focal length from 45 mm to 46 mm, a variation in the z position on the eye 20 of 2 mm can be obtained. The scale between the intermediate image 6 and the image field 17-1 on the eye 20 changes from −4 to −3.9 thereby. With a scanning lens 5 having a focal length of 70 mm, the necessary deflection angle on the x-y scanning unit 4 changes from 11.36° to 11.08°, which is compensated for by a corresponding change in the activation of the x-y scanning unit 4.

The features of the invention specified above and explained in various example embodiments can be used not only in the combinations specified by way of example, but also in other combinations or in and of themselves, without abandoning the scope of the present invention.

A description in reference to a device feature applies analogously to this feature for the corresponding method, while method features depict corresponding functional features of the described device.

The invention claimed is:

1. An ophthalmological laser therapy device having an optical axis that includes a laser system that generates a therapy laser beam and, in a beam path of the therapy laser beam, comprises:
   an x-y scanning unit configured to deflect the therapy laser beam perpendicular to the optical axis;
   collecting optics, comprising one or more lens elements, and having an axis of symmetry, which is identical to the optical axis, configured for mapping the therapy laser beam in an image field that is scanned by the x-y scanning unit;
   a scanning lens, configured to generate an intermediate image of the image field in an intermediate image plane between the collecting optics and the scanning lens, wherein the scanning lens focuses the light arriving from the x-y scanning unit in the intermediate image plane;
   a z scanning device that shifts the focal point of the therapy laser beam in a z direction along the optical axis; and
   an adjustable laser beam deflection device, which is disposed in the beam path of the therapy laser beam downstream of the x-y scanning unit, the z scanning device and the collecting optics, wherein the adjustable laser beam deflection device shifts the image field scanned by the x-y scanning unit over a working field in a region of tissue of a volume of the eye, the working field being larger than the image field.

2. The ophthalmological laser therapy device according to claim 1, in which the adjustable laser beam deflection device comprises a partial or fully reflective surface and two axes that are perpendicular to one another, wherein the partial or fully reflective surface can be pivoted about one or both of the axes that are perpendicular to one another.

3. The ophthalmological laser therapy device according to claim 2, wherein the partial or fully reflective surface comprises a beam splitter plate or a mirror.

4. The ophthalmological laser therapy device according to claim 2, wherein the adjustable laser beam deflection device comprises at least one refractive optical element with spherical surfaces, which is disposed downstream of the partial or fully reflective surface.

5. The ophthalmological laser therapy device according to claim 1, wherein the laser system comprises a femtosecond laser (fs) laser system.

6. The ophthalmological laser therapy device according to claim 1, wherein the Z scanning device comprises collecting optics that can be displaced as a unit in the z direction or includes one or more lenses that can be displaced in the z direction.

7. The ophthalmological laser therapy device according to claim 1, wherein the collecting optics can be displaced as a unit in the z direction or comprises one or more lenses that can be displaced in the z direction in addition to the z scanning device.

8. The ophthalmological laser therapy device according to claim 1, wherein the collecting optics is corrected for an image field having a diameter of less than 7 mm.

9. The ophthalmological laser therapy device according to claim 1, wherein the collecting optics is corrected for an image field having a diameter in a range of 4 to 7 mm.

10. The ophthalmological laser therapy device according to claim 1, wherein the x-y scanning unit comprises two galvanometer scanners disposed one directly following another, or a biaxial scanner, or two scanners having pupil mapping.

11. The ophthalmological laser therapy device according to claim 1, wherein the collecting optics is configured to generate an image field in a reduction by at least a factor of two of the intermediate image.

12. The ophthalmological laser therapy device according to claim 1, wherein the collecting optics is configured to generate an image field in a reduction by a factor of four, of the intermediate image.

13. The ophthalmological laser therapy device according to claim 1, wherein a correction factor is applied to at least one scanning angle of the x-y scanning unit to compensate for a change in a reduction of the intermediate image by the collecting optics during z scanning.

14. The ophthalmological laser therapy device according to claim 1, configured to decouple light into an observation beam path.

15. The ophthalmological laser therapy device according to claim 1, further comprising a device that generates an aiming beam to facilitate focusing and lateral alignment of the therapy laser beam.

16. The ophthalmological laser therapy device according to claim 15, wherein the aiming beam focus and the therapy beam focus are offset axially to one another.

17. A method for treating a tissue of an eye, a material located in an eye or both by application of a therapy laser beam with an ophthalmological laser therapy device, comprising:

deflecting a beam path of the therapy laser beam using an adjustable laser beam deflection device, while the therapy laser beam is switched off, to a position such that a first sub-region of the tissue of the eye, the material located in the eye or both is located in an image field of collecting optics;

treating the first sub-region of the tissue of the eye, the material located in the eye or both with the therapy laser beam by application of:
  a series of quick x-y scans by operation of an x-y scanning unit distinct from the adjustable laser beam deflection device, and
  a single, slow z scan by operation of a z scanning unit distinct from the adjustable laser beam deflection device;

generating an intermediate image of the image field in an intermediate image plane between the collecting optics and a scanning lens, by focusing light arriving from the x-y scanning unit in the intermediate image plane; and carrying out the deflecting the beam path of the therapy laser beam and the treating for further sub-regions of the tissue of the eye, the material located in the eye or both, until the tissue of the eye, the material located in the eye or both have been fully treated.

18. The method according to claim 17, wherein, when a maximum expansion of the tissue of the eye, the material located in the eye or both that is to be treated, is smaller than a diameter of the image field of the collecting optics, further comprising fixing the adjustable laser beam deflection device in a position such that of the tissue of eye, the material located in the eye or both to be treated are located simultaneously and entirely in the image field of the collecting optics.

* * * * *

UNITED STATES PATENT AND TRADEMARK OFFICE
CERTIFICATE OF CORRECTION

PATENT NO. : 11,039,956 B2  
APPLICATION NO. : 15/561894  
DATED : June 22, 2021  
INVENTOR(S) : Beate Böhme et al.

Page 1 of 1

It is certified that error appears in the above-identified patent and that said Letters Patent is hereby corrected as shown below:

On the Title Page

Item (57), in the Abstract, Line 15:
Delete "or" and insert --of--

Signed and Sealed this
Fifteenth Day of March, 2022

Drew Hirshfeld
*Performing the Functions and Duties of the*
*Under Secretary of Commerce for Intellectual Property and*
*Director of the United States Patent and Trademark Office*